United States Patent [19]

Hoffman et al.

[11] Patent Number: 4,857,547
[45] Date of Patent: Aug. 15, 1989

[54] NOVEL HMG-COA REDUCTASE INHIBITORS

[75] Inventors: William F. Hoffman; Ta J. Lee, both of Lansdale, Pa.

[73] Assignee: Merck & Co., Inc., Rahway, N.J.

[21] Appl. No.: 142,377

[22] Filed: Jan. 7, 1988

[51] Int. Cl.$^4$ .................. A61K 31/365; C07D 309/30
[52] U.S. Cl. .................... 514/460; 549/292; 544/59; 544/60; 544/149; 544/171; 544/172; 544/173; 544/359; 544/389; 546/207; 546/245; 548/517; 548/531
[58] Field of Search ............... 514/460, 510; 549/292; 560/119

[56] References Cited

U.S. PATENT DOCUMENTS 4,444,784  4/1984  Hoffman et al. .......... 549/292
4,661,483  4/1987  Hoffman et al. .......... 549/292

Primary Examiner—Glennon H. Hollrah
Assistant Examiner—Ba Trinh
Attorney, Agent, or Firm—Melvin Winokur; Joseph F. DiPrima

[57] ABSTRACT

Novel 3-hydroxy-3-methylglutaryl-coenzyme A (HMG-CoA) reductase inhibitors are useful as antihypercholesterolemic agents and are represented by the following general structural formulae (I) and (II):

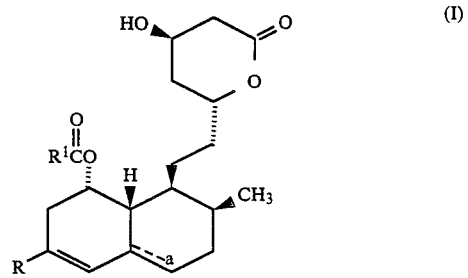

(I)

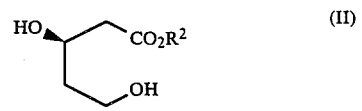

(II)

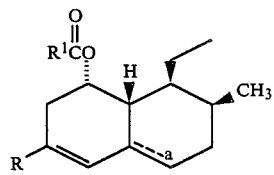

16 Claims, No Drawings

NOVEL HMG-COA REDUCTASE INHIBITORS

BACKGROUND OF THE INVENTION

Hypercholesterolemia is known to be one of the prime risk factors for atherosclerosis and coronary heart disease, the leading cause of death and disability in Western countries. The bile acid sequestrants seem to be moderately effective but they must be consumed in large quantities, i.e., several grams at a time, and they are not very palatable.

There are agents known, however, that are very active antihypercholesterolemic agents which function by limiting cholesterol biosynthesis via inhibiting the enzyme, HMG-CoA reductase. These agents include the natural fermentation products, such as mevastatin, lovastatin and pravastatin, and semisynthetic analogs, such as simvastatin. These compounds have the following chemical structural formulae:

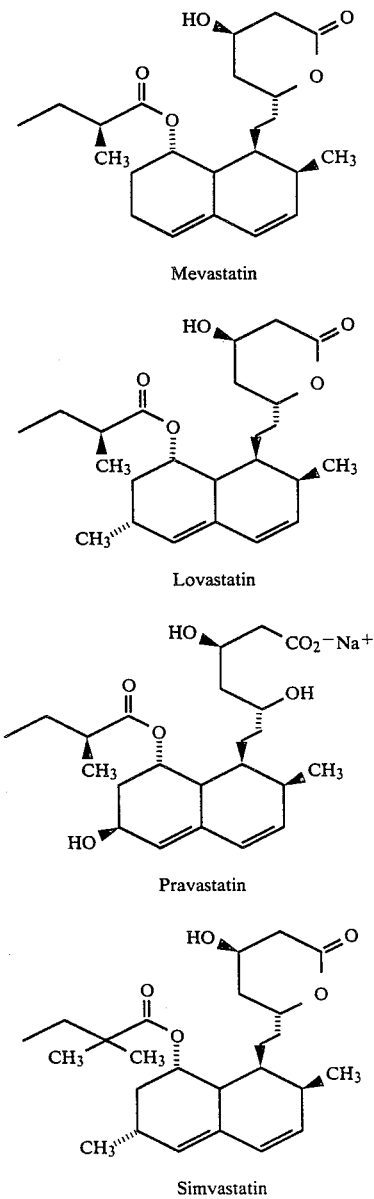

Recently, Mevacor ®, which contains lovastatin as the active agent, was approved by the Food and Drug Administration for use as an antihypercholesterolemic drug.

Numerous analogs and homologs of these compounds have been described in the patent literature. U.S. Pat. No. 4,444,784 disclosed analogs of lovastatin which possess polyhydronaphthyl moieties and various 8-acyloxy groups attached thereto. U.S. Pat. No. 4,661,483 also discloses analogs of lovastatin wherein the 8-acyloxy group has been elaborated. Additionally, co-pending U.S. applications Ser. Nos. 859,513, 859,524, 859,525, 859,530, 859,534, and 859,535 all filed on May 5, 1986, disclose further analogs of lovastatin which have functionalized 8-acyloxy groups. All of the lovastatin analogs, including simvastatin, which contain a 6-methyl group have that substituent in the natural 6α (axial) configuration.

Co-pending U.S. patent application Ser. No. 048,136 filed May 15, 1987, discloses compounds which are analogs of lovastatin and related compounds which possess a hydroxymethyl group, acyloxymethyl group, carbamoyloxymethyl group, a carboxy group, an alkoxycarbonyl group or a carbamoyl group substituted on the 6-position of the polyhydronaphthyl moiety. The compounds in this application may possess a substituent in the 6-position in either the 6α or 6β stereochemical position.

Co-pending U.S. patent application Ser. No. 092,354 filed Sept. 2, 1987, discloses compounds which are analogs of lovastatin and related compounds which possess a methyl group in the 6-position in the 6β stereochemical position.

SUMMARY OF THE INVENTION

This invention relates to novel compounds which are HMG-CoA reductase inhibitors and are useful as antihypercholesterolemic agents. Specifically, the compounds of this invention are analogs of lovastatin and related compounds which contain two double bonds in the 4,4a- and 5,6-positions or a double bond in the 5,6-position of the polyhydronaphthyl moiety. Additionally, pharmaceutical compositions of these novel compounds, as the sole therapeutically active ingredient and in combination with bile acid sequestrants, are disclosed. Other embodiments of this invention are methods of treating disease conditions in which hypercholesterolemia is an etiological factor, and processes for preparing the novel compounds.

DETAILED DESCRIPTION OF THE INVENTION

The specific HMG-CoA reductase inhibitors of this invention are the compounds represented by the following general structural formulae (I) and (II):

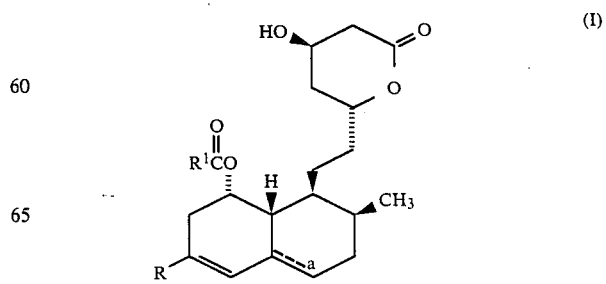

(I)

-continued

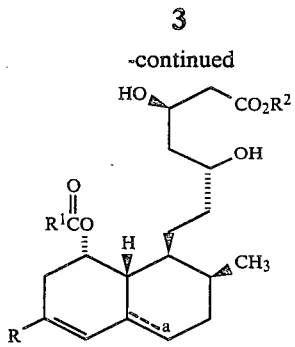
(II)

wherein:
R is $CH_2OH$,

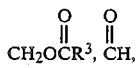

or $CO_2R^4$;

$R^1$ and $R^3$ are independently selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

$R^2$ and $R^4$ are independently selected from
(a) hydrogen;
(b) $C_{1-5}$ alkyl;
(c) substituted-$C_{1-5}$ alkyl in which the substituent is selected from
 (i) phenyl,
 (ii) dimethylamino, and
 (iii) acetylamino; and
(d) 2,3-dihydroxypropyl;

X and Y independently are hydrogen, halogen, trifluoromethyl, $C_{1-3}$ alkyl, nitro, cyano or group selected from:
(1) $R^8O(CH_2)_m$ in which m is 0 to 3 and $R^8$ is hydrogen, $C_{1-3}$alkyl or hydroxy-$C_{2-3}$alkyl;
(2)

in which $R^9$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$ alkylamino-$C_{1-3}$alkyl or di(hydroxy-$C_{2-3}$alkyl)amino-$C_{1-3}$alkyl;
(3)

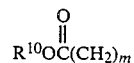

in which $R^{10}$ is hydrogen, $C_{1-3}$alkyl, hydroxy-$C_{2-3}$ alkyl, $C_{1-3}$alkoxy-$C_{1-3}$alkyl, phenyl or naphthyl;
(4) $R^{11}R^{12}N(CH_2)_m$,

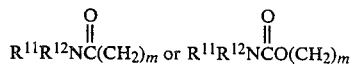

in which $R^{11}$ and $R^{12}$ independently are hydrogen, $C_{1-3}$ alkyl, hydroxy-$C_{2-3}$alkyl or together with the nitrogen atom to which they are attached form a heterocyclic group selected from piperidinyl, pyrrolidinyl, piperazinyl, morpholinyl or thiomorpholinyl;
(5) $R^{13}S(O)_n(CH_2)m$ in which $R^{13}$ is hydrogen, $C_{1-3}$alkyl, amino, $C_{1-3}$alkylamino or di($C_{1-3}$alkyl)amino;

a represents a single bond or a double bond; or a pharmaceutically acceptable salt thereof.

Except where specifically defined to the contrary, the terms "alkyl", "alkoxy" and "acyl" include both the straight-chain and branched-chain species of the term.

One embodiment of this invention is the class of compounds of the formulae (I) and (II) wherein:
R is $CH_2OH$,

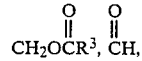

or $CO_2R^4$;

$R^1$ is selected from:
(1) $C_{1-10}$ alkyl;
(2) $C_{3-8}$ cycloalkyl;

$R^3$ is selected from:
(1) $C_{1-10}$ alkyl;
(2) $C_{3-8}$ cycloalkyl;
(3) phenylamino; and
(4) substituted phenylamino in which the substituents are X and Y;

$R^4$ is hydrogen; and
a is a double bond.

One subclass of this embodiment is the compounds of the formulae (I) and (II) wherein:
R is CH$_2$OH; and
R$^1$ is C$_{1-10}$ alkyl.

Exemplifying this subclass are the following compounds of the formulae (I) and (II): 6(R)-[2-[8(S)-(2,2-dimethylbutyryloxy)-2(S)-methyl-6-hydroxymethyl-1,2,3,7,8,8a(R)-hexahydronaphthyl-1(S)]-ethyl]-4(R)-hydroxy-3,4,5,6-tetrahydro-2H-pyran-2-one; and
the corresponding ring opened dihydroxy acids and esters thereof.

A second subclass of this embodiment is the compounds of the formulae (I) and (II) wherein:
R is CO$_2$H; and
R$^1$ is C$_{1-10}$ alkyl.

Exemplifying this subclass are the following compounds of the formulae (I) and (II): 6(R)-[2-[8(S)-(2,2-dimethylbutyryloxy)-2(S)-methyl-6-carboxy-1,2,3,7,8,8a(R)-hexahydronaphthyl-1(S)]-ethyl]-4(R)-hydroxy-3,4,5,6-tetrahydro-2H-pyran-2-one; and
the corresponding ring opened dihydroxy acids and esters thereof.

A third subclass of this embodiment is the compounds of the formulae (I) and (II) wherein:
R is

R$^1$ is C$_{1-10}$ alkyl; and
R$^3$ is phenylamino.

Exemplifying this subclass are the following compounds of the formulae (I) and (II): 6(R)-[2-[8(S)-(2,2-dimethylbutyryloxy)-2(S)-methyl-6-phenylaminocarbonyloxymethyl-1,2,3,7,8,8a(R)-hexahydronaphthyl-1(S)]-ethyl]-4(R)-hydroxy-3,4,5,6-tetrahydro-2H-pyran-2-one; and
the corresponding ring opened dihydroxy acids and esters thereof.

A forth subclass of this embodiment is the compounds of the formulae (I) and (II) wherein:
R is

and
R$^1$ is C$_{1-10}$ alkyl.

Exemplifying this subclass are the following compounds of the formulae (I) and (II): 6(R)-[2-[8(S)-(2,2-dimethylbutyryloxy)-2(S)-methyl-6-formyl-1,2,3,7,8,8a(R)-hexahydronaphthyl-1(S)]-ethyl]-4(R)-hydroxy-3,4,5,6-tetrahydro-2H-pyran-2-one; and
the corresponding ring opened dihydroxy acids and esters thereof.

A second embodiment of this invention is the class of compounds of the formulae (I) and (II) wherein:
R is CH$_2$OH,

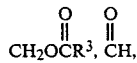

or CO$_2$R$^4$;
R$^1$ is selected from:
(1) C$_{1-10}$ alkyl;
(2) C$_{3-8}$ cycloalkyl;
R$^3$ is selected from:
(1) C$_{1-10}$ alkyl;
(2) C$_{3-8}$ cycloalkyl;
(3) phenylamino; and
(4) substituted phenylamino in which the substituents are X and Y;
R$^4$ is hydrogen; and
a is a single bond.

The compounds of formula (I) are conveniently prepared from 6(R)-[2-[8(S)-acyloxy-2(S),6(R)-dimethyl-4a(S)-hydroxy-5(S)-chloro-1,2,4a,5,6,7,8,8a(S)-octahydronaphthyl-1(S)]ethyl]-4(R)-trialkysilyloxy-3,4,5,6-tetrahydro-2H-pyran-2-one, exemplified here as 6(R)-[2-[8(S)-(2,2-dimethylbutyryloxy)-2(S), 6(R)-dimethyl-4a(S)-hydroxy-5(S)-chloro-1,2,4a,5,6,7,8,8a(S)-octahydronaphthyl-1(S)]-ethyl]-4(R)-t-butyldimethylsilyloxy-3,4,5,6-tetrahydro-2H-pyran-2-one, which may be prepared according to the general procedures described in co-pending U.S. patent application, Ser. No. 131,695, filed Dec. 11, 1987, via the following synthetic pathways:

Pathway A

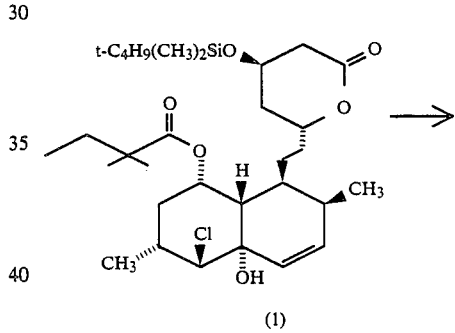

(1)

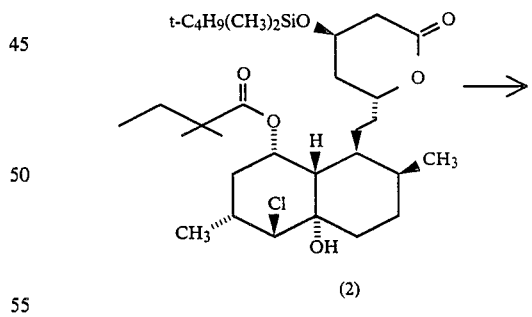

(2)

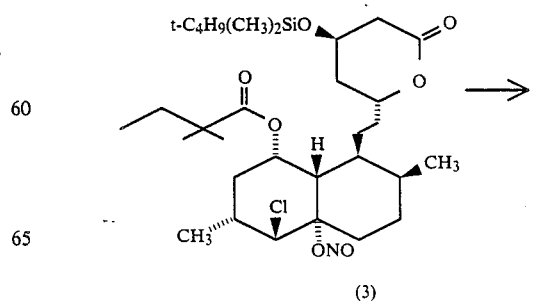

(3)

-continued
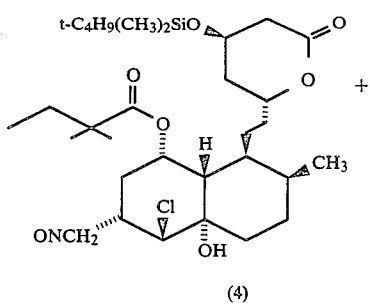
(4)
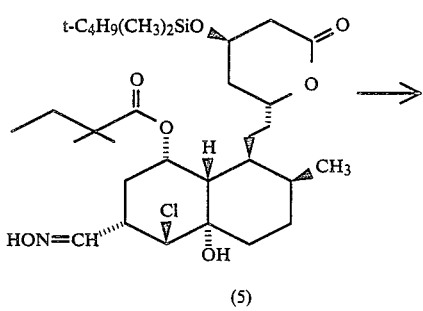
(5)
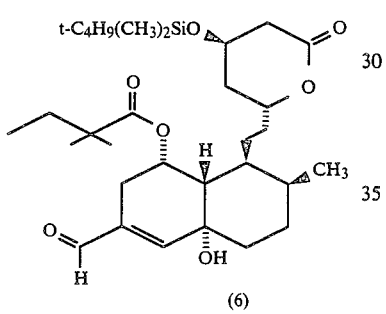
(6)
Pathway B
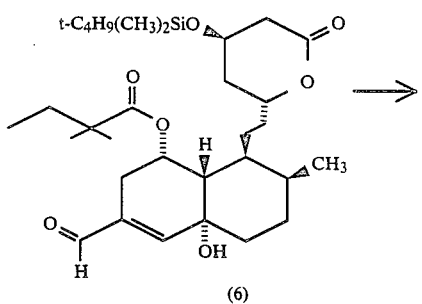
(6)
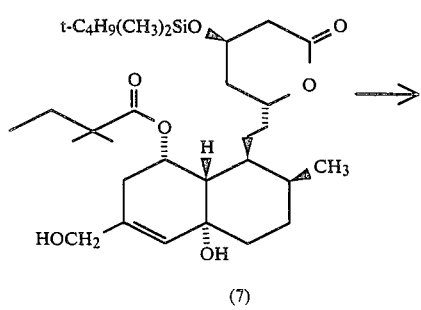
(7)
-continued
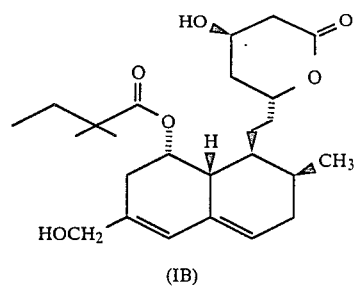
(IB)
Pathway C
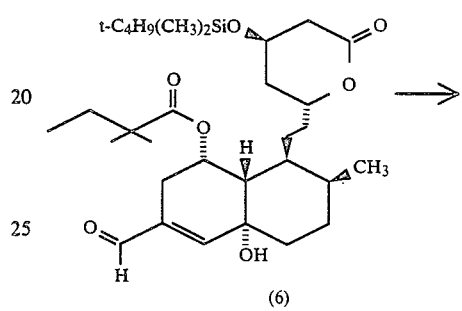
(6)
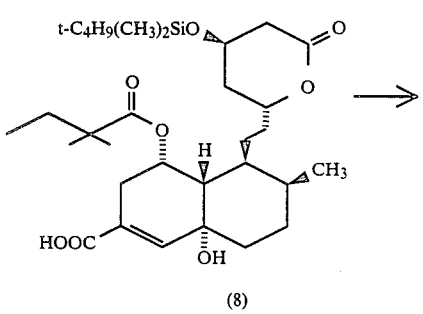
(8)
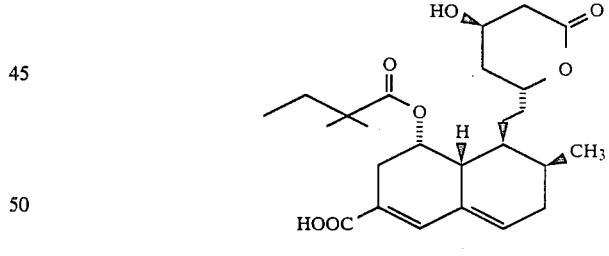
(IC)
Pathway D
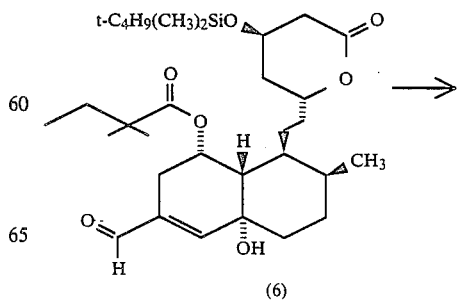
(6)

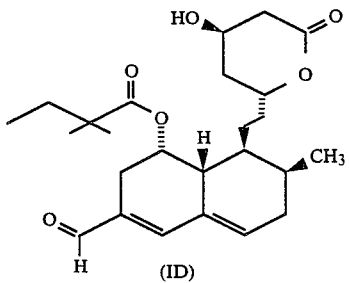

(ID)

Pathway E

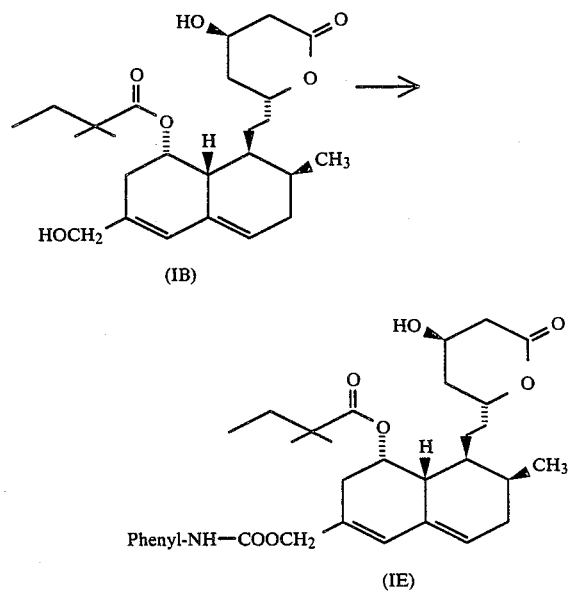

(IB)

(IE)

As shown in Pathway A, 6(R)-[2-[8(S)-(2,2-dimethylbutyryloxy)-2(S), 6(R)-dimethyl-4a(S)-hydroxy-5(S)-cloro-1,2,4a,5,6,7,8,8a(S)-octahydronaphthyl-1(S)]-ethyl]-4(R)-t-butyldimethylsilyloxy-3,4,5,6-tetrahydro-2H-pyran-2-one, Compound 1, is hydrogenated to yield the decahydro analog, Compound 2, under standard conditions over a rhodium on carbon catalyst. Compound 2 is treated with nitrosyl chloride at low temperature in an organic base to give Compound 3. A solution of Compound 3 is then irradiated under standard Barton reaction conditions to afford a mixture of Compound 4 and Compound 5. Compound 4 in a mixture is converted into Compound 5 upon treatment with alcohol and an organic base. Compound 5 is reacted with sodium nitrite and then aqueous acetic acid to yield after a silica gel isolation step the formyl intermediate, Compound 6.

To prepare the compounds of formula (I) wherein R is CH$_2$OH and a is a double bond, as shown in Pathway B, the Compound 6 is reduced under standard conditions with sodium borohydride to yield the Compound 7 which is then treated with hydrofluoric acid to remove the trialkylsilyl protecting group and introduce the 4,4a double bond to afford the desired product.

To prepare the compounds of formula (I) wherein R is CO$_2$H and a is a double bond, as shown in Pathway C, the Compound 6 dissolved in t-butyl alcohol with a trace of 2-methyl-2-butene is treated with sodium chlorite and sodium dihydrogenphosphate to give Compound 8 which is then treated with hydrofluoric acid under standard conditions to remove the trialkylsilyl protecting group and introduce the 4,4a double bond to afford the desired product.

To prepare the compounds of formula (I) wherein R is

and a is a double bond, as shown in Pathway D, the Compound 6 is simply treated with hydrofluoric acid to remove the trialkylsilyl protecting group and introduce the 4,4a double bond to afford the desired product. Alternatively, the Compound 6 may be treated with methanesulfonyl chloride and triethylamine to give the desired product. It should be noted that the desired product can be reduced under standard conditions with sodium borohydride to give the compound of formula (I) wherein R is CH$_2$OH and a is a double bond.

To prepare the compounds of formula (I) wherein R is

R$^3$ is phenylamino and a is a double bond, as shown in Pathway E, the compound of the formula (I) wherein R is CH$_2$OH and a is a double bond is reacted with phenylisocyanate to afford the desired product.

To prepare the compounds of formula (I) wherein R is a is a single bond, the compound IB can be hydrogenated in the presence of Crabtree catalyst to give the compound of the formula (I) wherein R is CH$_2$OH and a is a single bond, which is then oxidized utilizing the Swern modification of the Moffatt oxidation reaction to give the corresponding aldehyde. From these compounds, the compounds of the formula (I) wherein a is a single bond are readily obtained using standard chemical transformations.

Where the product formed by the above described synthetic pathways is not the desired form of that compound, then that product may be subjected to one or more further reactions such as hydrolysis, salification, esterification, acylation, ammonolysis or lactonization by conventional methods, as described in more detail hereafter.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, histidine, α, β-diaminobutyric acid or ornithine.

Preferred amines to form amine salts include t-octylamine, dibenzylamine, dichlorohexylamine, morpholine, alkyl esters of D-phenylglycine and D-glucosamine. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl-C$_{1-5}$alkyl, dimethylamino-C$_{1-5}$alkyl, or acetylamino-C$_{1-5}$alkyl may be employed if desired.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic ether (such as THF) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction; suitable solvents include benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347–358 (1985).

For estimation of relative inhibitory potencies, compactin (i.e., mevastatin) was assigned a value of 100 and the $IC_{50}$ value of the test compound was compared with that of mevastatin (compactin) determined simultaneously in the published in vitro protocol.

Representative of the intrinsic HMG-CoA reductase inhibitory activities of the claimed compounds are the relative potencies tabulated below for a number of the claimed compounds.

| R | $R^1$ | a | Relative Potency |
|---|---|---|---|
| $CH_2OH$ | 1,1-dimethylpropyl | db | 75 |
| $CO_2H$ | 1,1-dimethylpropyl | db | 100 |
| PhNHCOCH$_2$ (O=) | 1,1-dimethylpropyl | db | 200 | db = double bond

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in an non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-(2,2-dimethylbutyryloxy)-2(S)-methyl-6-hydroxymethyl-1,2,3,7,8,8a(R)-hexahydronaphthyl-1(S)]-ethyl]-4(R)-hydroxy-3,4,5,6-tetrahydro-2H-pyran-2-one (IB)

(a) 6(R)-[2-[8(S)-(2,2-dimethylbutyryloxy)-2(S),6(R)-dimethyl-4a(S)-hydroxy-5(S)-chloro-1,2,3,4,4a,5,6,7,8,8a(S)-decahydronaphthyl-1(S)]ethyl]-4(R)-t-butyldimethylsilyloxy-3,4,5,6-tetrahydro-2H-pyran-2-one (2)

To 6(R)-[2-[8(S)-(2,2-dimethylbutyryloxy)-2(S),6(R)-dimethyl-4a(S)-hydroxy-5(S)-chloro-1,2,4a,5,6,7,8,8a(S)-octahydronaphthyl-1(S)]ethyl]-4(R)-t-butyl-dimethylsilyloxy-3,4,5,6-tetrahydro-2H-pyran-2-one 1 (4.95 g, 8.46 mmol), dissolved in ethyl acetate (150 ml), was added rhodium on carbon catalyst (400 mg) and the mixture was hydrogenated on the Roche-Kuhner Typ NDH for 5 hours until hydrogen uptake stopped. The reaction mixture was filtered and the filtrate concentrated to yield a colorless solid which was purified by flash chromatography eluted with 20 percent ethyl acetate in hexane to yield the title compound: mp 139–140 C.

Elemental analysis for $C_{31}H_{55}ClO_6Si$: Calc'd C, 63.39; H, 9.44; Found C, 63.25; H, 9.76.

(b) 6(R)-[2-[8(S)-(2,2-dimethylbutyryloxy)-2(S),6(R)-dimethyl-4a(S)-nitrosyloxy-5(S)-chloro-1,2,3,4,4a,5,6,7,8,8a(S)-decahydronaphthyl-1(S)]ethyl]-4(R)-t-butyldimethylsilyloxy-3,4,5,6-tetrahydro-2H-pyran-2-one (3)

Nitrosyl chloride gas was passed through a solution of compound 2 (2.0 g, 3.4 mmol) in pyridine (25 ml) at 0° C. for about 5 minutes. The reaction mixture was then poured into ice-water (200 ml) and benzene (100 ml). The aqueous layer was extracted with benzene (2×100 ml) and the combined organic phases were dried over $MgSO_4$. The mixture was filtered and used in the next step without further purification.

(c) 6(R)-[2-[8(S)-(2,2-dimethylbutyryloxy)-2(S)-methyl-4a(S)-hydroxy-5(S)-chloro-6(S)-hydroxyiminomethyl-1,2,3,4,4a,5,6,7,8,8a(S)-decahydronaphthyl-1(S)]ethyl]-4(R)-t-butyldimethylsilyloxy-3,4,5,6-tetrahydro-2H-pyran-2-one (5)

The benzene solution containing compound 3 (2.09 g, 3.40 mmol) was degassed with nitrogen for about ½ hour. The solution was irradiated (450 W Hanovia medium pressure mercury lamp, pyrex filter) for about 35 minutes. The reaction mixture was washed with 5 percent hydrochloric acid (3×50 ml), water (50 ml), saturated sodium bicarbonate (2×50 ml), brine (2×50 ml) and then dried over $MgSO_4$. The mixture was filtered and the filtrate concentrated in vacuo to afford a brown oil which contained the desired product and its 6-nitrosylmethyl precursor 4. The brown oil was dissolved in isopropanol (20 ml) and triethylamine (1 ml) was added. After approximately 21 hours at 50 C, the majority of the solvent was removed in vaccuo and the residue dissolved in diethyl ether (100 ml). The organic phase was washed with 5 percent hydrochloric acid (10 ml), water (10 ml), saturated sodium bicarbonate (25 ml), brine (2×25 ml) and then dried over $MgSO_4$. Filtration and evaporation gave a brown oil which was purified by flash column chromatography over silica gel eluted with 5 percent isopropanol in hexane (500 ml), 7.5 percent isopropanol in hexane (1500 ml), and then 10 percent isopropanol in hexane (1500 ml) to afford the desired compound.

(d) 6(R)-[2-[8(S)-(2,2-dimethylbutyryloxy)-2(S)-methyl-4a(S)-hydroxy-6-formyl-1,2,3,4,4a,7,8,8a(S)-octahydronaphthyl-1(S)ethyl]-4(R)-t-butyl-dimethylsilyloxy-3,4,5,6-tetrahydro-2H-pyran-2-one (6)

A solution of the compound 5 (1.06 g, 1.72 mmol) in acetic acid (20 ml) and water (10 ml) was cooled to 0° C. and sodium nitrite (1.18 g, 17.2 mmol) was added. The reaction mixture was stirred at 0° C. for about ½ hour and then at ambient temperature for about 1 hour. The reaction mixture was then poured into diethyl ether (200 ml), washed with water (50 ml) and then carefully washed with saturated sodium bicarbonate (until the wash was basic to litmus), and brine (50 ml). The reaction mixture was then dried over $MgSO_4$, filtered and evaporated to give the crude lactol. Upon flash column chromatography over silica gel eluted with 15 percent ethyl acetate in hexane (2 L), and then 25 percent ethyl acetate in hexane, the lactol converted to give the desired compound.

(e) 6(R)-[2-[8(S)-(2,2-dimethylbutyryloxy)-2(S)-methyl-4a(S)-hydroxy-6-hydroxymethyl-1,2,3,4,4a,7,8,8a(S)-octahydronaphthyl-1(S)]ethyl]-4(R)-t-butyldimethylsilyloxy-3,4,5,6-tetrahydro-2H-pyran-2-one (7)

To a solution of compound 6 (53.6 mg, 0.1 mmol) in THF (5 ml) was added sodium borohydride (3.8 mg, 0.1 mmol) and the stirred solution was cooled in an ice bath. Water (1 ml) was then added and the mixture stirred for about ½ hour. Saturated $NH_4Cl$ (5 ml) was then added and the reaction mixture extracted wih diethyl ether (3×50 ml). The combined extracts were washed with brine (25 ml) and dried over $MgSO_4$. Filtration and evaporation gave the compound as a colorless oil which was used in the next step without further purification.

(f) 6(R)-[2-[8(S)-(2,2-dimethylbutyryloxy)-2(S)-methyl-6-hydroxymethyl-1,2,3,7,8,8a(R)-hexahydronaphthyl-1(S)]ethyl]-4(R)-hydroxy-3,4,5,6-tetrahydro-2H-pyran-2-one (IB)

To a solution of the compound 7 (53 mg, 0.098 mmol) in acetonitrile (5 ml) was added 48 percent hydrofluoric acid in acetonitrile (5 ml, 1:19:V:V) and the reaction mixture stirred at ambient temperature for about 2 hours. The reaction mixture was poured into diethyl ether (100 ml) and the ethereal solution washed with saturated sodium bicarbonate (2×10 ml), brine (2×20 ml) and dried over $MgSO_4$. Filtration and evaporation gave a viscous oil which was purified by flash column chromatography over silica gel eluted with 20 percent isopropanol in hexane (2 column volumes) and 40 percent isopropanol in hexane to afford the desired product.

Alternate preparation of
6(R)-[2-[8(S)-(2,2-dimethylbutyryloxy)-2(S)-methyl-6-hydroxymethyl-1,2,3,7,8,8a(R)-hexahydronaphthyl-1(S)]-ethyl]-4(R)-hydroxy-3,4,5,6-tetrahydro-2H-pyran-2-one (IB)

To a solution of the compound ID from Example 3 (95 mg, 0.219 mmol) in 95 percent ethanol (10 ml) cooled in an ice/water bath was added sodium borohydride (8.3 mg, 0.219 mmol) dissolved in a small amount of 95 percent ethanol. After 25 minutes, saturated aqueous $NH_4Cl$ (5 ml) was added and the reaction mixture partitioned between diethyl ether (100 ml) and water (10 ml). The aqueous layer was extracted with diethyl ether (50 ml) and the combined ethereal extracts were washed with brine (25 ml) and then dried over $MgSO_4$. Filtration and evaporation gave a viscous oil which was purified by flash column chromatography over silica gel eluted with 20 percent isopropanol in hexane to yield the desired compound as an amorphous solid.

Elemental analysis for $C_{25}H_{38}O_6$: Calc'd C, 69.09; H, 8.81; Found C, 68.76; H, 8.87.

EXAMPLE 2

Preparation of
6(R)-[2-[8(S)-(2,2-dimethylbutyryloxy)-2(S)-methyl-6-carboxy-1,2,3,7,8,8a(R)-hexahydronaphthyl-1(S)]-ethyl]-4(R)-hydroxy-3,4,5,6-tetrahydro-2H-pyran-2-one (IC)

(a) 6(R)-[2-[8(S)-(2,2-dimethylbutyryloxy)-2(S)-methyl-4a(S)-hydroxy-6-carboxy-1,2,3,4,4a,7,8,8a(S)-octahydronaphthyl-1(S)]-ethyl]-4(R)-t-butyldimethylsilyloxy-3,4,5,6-tetrahydro-2H-pyran-2-one (8)

To a solution of the compound 6 (53 mg, 0.1 mmol) in t-butyl alcohol (2 ml) and 2-methyl-2-butene (0.6 ml) was added dropwise a solution of sodium chlorite (100 mg) and sodium dihydrogenphosphate (114 mg) in water (1 ml). After about ½ hour at ambient temperature, the solvent was removed in vacuo and the residue dissolved in a small amount of water. The mixture was extracted with diethyl ether (3×50 ml) and the combined extracts were washed with brine (2×25 ml) and the dried over MgSO$_4$. Filtration and evaporation gave the desired compound as a pale yellow oil which was used in the next step without further purification.

(b) 6(R)-[2-[8(S)-(2,2-dimethylbutyryloxy)-2(S)-methyl-6-carboxy-1,2,3,7,8,8a(R)-hexahydronaphthyl-1(S)]ethyl]-4(R)-hydroxy-3,4,5,6-tetrahydro-2H-pyran-2-one (IC)

To a solution of the compound 8 (45 mg) in acetonitrile (5 ml) was added 48 percent hydrofluoric acid in acetonitrile (5 ml, 1:19:V:V) and the reaction mixture stirred at ambient temperature for about 2 hours. The solution was poured into diethyl ether (100 ml) and was washed with water (2×50 ml) and then dried over MgSO$_4$. Filtration and evaporation gave a viscous oil which was purified by flash column chromatography over silica gel eluted with ethyl acetate:pyridine:acetic acid:water (30:5:1:1) to afford a colorless foam. Further high pressure liquid chromatography on a C$_8$ Altex column eluted with 25 percent acetonitrile in water yielded the desired compound as an amorphous solid.

Elemental analysis for $C_{25}H_{36}O_7 \cdot 1\frac{1}{2} H_2O$: Calc'd C, 63.11; H, 8.27; Found C, 63.38; H, 8.07.

EXAMPLE 3

Preparation of 6(R)-[2-[8(S)-(2,2-dimethylbutyryloxy)-2(S)-methyl-6-formyl-1,2,3,7,8,8a(R)-hexahydronaphthyl-1(S)]-ethyl]-4(R)-hydroxy-3,4,5,6-tetrahydro-2H-pyran-2-one (ID)

To a solution of the compound 6 (216 mg) in acetonitrile (9 ml) was added 48 percent hydrofluoric acid in acetonitrile (20 ml, 1:19:V:V) and the reaction mixture stirred at ambient temperature for about six hours. The reaction mixture was then poured into diethyl ether (200 ml) and was washed with water (20 ml), saturated sodium bicarbonate (20 ml), brine (2×20 ml) and then dried over MgSO$_4$. Filtration and evaporation gave a viscous oil which was purified by flash column chromatography over silica gel eluted with 20 percent isopropanol in hexane to afford the desired compound as colorless oil.

$^1$H NMR (CDCl$_3$) δ 0.73 (3H, t, J=7 Hz), 0.86 (3H, d, J=7 Hz), 1.03 (3H, s), 1.05 (3H, s), 4.38 (H, m), 4.66 (H, m), 5.52 (H, m), 6.22 (H, m), 6.95 (H, m), 9.51 (H, s).

EXAMPLE 4

Preparation of 6(R)-[2-[8(S)-(2,2-dimethylbutyryloxy)-2(S)-methyl-6-phenylaminocarbonyloxymethyl-1,2,3,7,8,8a(R)-hexahydronaphthyl-1(S)]-ethyl]-4(R)-hydroxy-3,4,5,6-tetrahydro-2H-pyran-2-one (IE)

To a solution of the compound IB (15 mg, 0.0345 mmol) in pyridine (1 ml) was added phenylisocyanate (4.1 mg, 0.345 mmol) at ambient temperature and the reaction mixture stirred for about 16 hours. Additional phenylisocyanate (4 μl) was added and the reaction mixture heated to 60° C. for an hour. Phenylisocyanate (10 μl) was again added and the reaction mixture heated to 60° C. for an additional hour. This was repeated once more and then the reaction mixture was poured into diethyl ether (50 ml). The solution was washed with 1N hydrochloric acid (3×5 ml), water (5 ml), saturated sodium bicarbonate (5 ml), brine (2×5 ml) and dried over MgSO$_4$. Filtration and evaporation gave a viscous oil which was purified by flash column chromatography over silica gel eluted with 20 percent isopropanol in hexane to afford the desired compound as colorless foam. The foam was dissolved in diethyl ether, filtered and evaporated to give the desired compound as a viscous oil which solidified on standing (mp. 58°–61° C.).

Elemental analysis for $C_{32}H_{43}NO_7$: Calc'd C, 69.41; H, 7.82; N, 2.53; Found C, 69.22; H, 8.12; N, 2.34.

EXAMPLES 5 to 12

Utlizing the general procedures described in Examples 1 to 4, the following compounds of the formula (I) are prepared from the appropriately substituted starting materials and reactants.

| Compound No. | R | R$^1$ | a |
|---|---|---|---|
| 9 | CH$_2$OH | sec-butyl | db |
| 10 | CO$_2$H | sec-butyl | db |
| 11 | CHO | sec-butyl | db |
| 12 | CH$_2$OCNHPh (O=) | sec-butyl | db |
| 13 | CH$_2$OH | sec-butyl | sb |
| 14 | CO$_2$H | 1,1-dimethyl-propyl | sb |
| 15 | CHO | sec-butyl | sb |
| 16 | CH$_2$OCNHPh (O=) | 1,1-dimethyl propyl | sb | sb = single bond, and db = double bond

EXAMPLE 13

Preparation of Ammonium Salts of Compounds II

The lactone (1.0 mmol) from Example 1 is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give a gum which solidified to provide the ammonium salt.

EXAMPLE 14

Preparation of Alkali and Alkaline Earth Salts of Compounds II

To a solution of 42 mg of lactone from Example 1 in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 15

Preparation of Ethylenediamine Salts of Compounds II

To a solution of 0.50 g of the ammonium salt from Example 13 in 10 ml of methanol is added 75 ml of ethylenediamine. The methanol is stripped off under vacuum to obtain the desired ethylenediamine salt.

EXAMPLE 16

Preparation of Tris(hydroxymethyl)aminomethane Salts of Compounds II

To a solution of 202 mg of the ammonium salt from Example 13 in 5 ml of methanol is added a solution of 60.5 mg of tris(hydroxymethyl) aminomethane in 5 ml of methanol. The solvent is removed in vacuo to afford the desired tris(hydroxymethyl)aminomethane salt.

EXAMPLE 17

Preparation of L-Lysine Salts of Compounds II

A solution of 0.001 mole of L-lysine and 0.0011 mole of the ammonium salt from Example 13 in 15 ml of 85% ethanol is concentrated to dryness in vacuo to give the desired L-lysine salt.

Similarly prepared are the L-arginine, L-ornithine, and N-methylglucamine salts.

EXAMPLE 18

Preparation of Tetramethylammonium Salts of Compounds II

A mixture of 68 mg of ammonium salt from Example 13 in 2 ml of methylene chloride and 0.08 ml of 24% tetramethylammonium hydroxide in methanol is diluted with ether to yield the desired tetramethylammonium salt.

EXAMPLE 19

Preparation of Methyl Esters of Compounds II

To a solution of 400 mg of lactone from Example 1 in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of propanol, butanol, isobutanol, t-butanol, amylalcohol, isoamylalcohol, 2,2-dimethylaminoethanol, benzylalcohol, phenethanol, 2-acetamidoethanol and the like, the corresponding esters are obtained.

EXAMPLE 20

Preparation of Free Dihydroxy Acids

The sodium salt of the compound II from Example 10 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding, parent lactone on standing.

EXAMPLE 21

As a specific embodiment of a composition of this invention, 20 mg of lactone from Example 1 is formulated with sufficient finely divided lactose to provide a total amount of 580 to 590 mg to fill a size 0, hard-gelatin capsule.

What is claimed is:

1. A compound represented by the following structural formula (I):

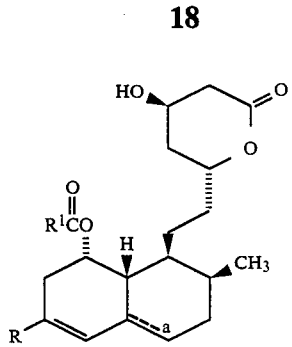

wherein:

R is $CH_2OH$,

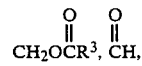

or $CO_2R^4$;

$R^1$ and $R^3$ are independently selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

$R^4$ is independently selected from
(a) hydrogen;
(b) $C_{1-5}$ alkyl;

(c) substituted-$C_{1-5}$ alkyl in which the substituent is selected from
(i) phenyl,
(ii) dimethylamino, and
(iii) acetylamino; and
(d) 2,3-dihydroxypropyl;
X and Y independently are hydrogen, halogen, trifluoromethyl, $C_{1-3}$ alkyl, nitro, cyano or group selected from:
(1) $R^8O(CH_2)_m$ in which m is 0 to 3 and $R^8$ is hydrogen, $C_{1-3}$alkyl or hydroxy-$C_{2-3}$alkyl;
(2)

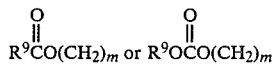

in which $R^9$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$ alkylamino-$C_{1-3}$alkyl or di(hydroxy-$C_{2-3}$alkyl) amino-$C_{1-3}$alkyl;
(3)

in which $R^{10}$ is hydrogen, $C_{1-3}$alkyl, hydroxy-$C_{2-3}$ alkyl, $C_{1-3}$alkoxy-$C_{1-3}$alkyl, phenyl or naphthyl;
(4) $R^{11}R^{12}N(CH_2)_m$,

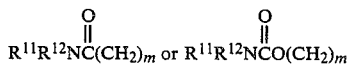

in which $R^{11}$ and $R^{12}$ independently are hydrogen,
(5) $R^{13}S(O)_n(CH_2)_m$ in which $R^{13}$ is hydrogen, $C_{1-3}$alkyl, amino, $C_{1-3}$alkylamino or di($C_{1-3}$alkyl)amino; and
a represents a single bond or a double bond; or a pharmaceutically acceptable salt thereof.

2. A compound of claim 1 wherein:
$R^1$ is selected from:
(1) $C_{1-10}$ alkyl;
(2) $C_{3-8}$ cycloalkyl;
$R^3$ is selected from:
(1) $C_{1-10}$ alkyl;
(2) $C_{3-8}$ cycloalkyl;
(3) phenylamino; and
(4) substituted phenylamino in which the substituents are X and Y;
$R^4$ is hydrogen; and
a is a double bond.

3. A compound of claim 2 wherein:
R is $CH_2OH$; and
$R^1$ is $C_{1-10}$ alkyl.

4. A compound of claim 3 which is 6(R)-[2-[8(S)-(2,2-dimethylbutyryloxy)-2(S)-methyl-6-hydroxymethyl-1,2,3,7,8,8a(R)-hexahydronaphthyl-1(S)]-ethyl]-4(R)-hydroxy-3,4,5,6-tetrahydro-2H-pyran-2one.

5. A compound of claim 2 wherein:
R is $CO_2H$; and
$R^1$ is $C_{1-10}$ alkyl.

6. A compound of claim 5 which is 6(R)-[2-[8(S)-(2,2-dimethylbutyryloxy)-2(S)-methyl-6-carboxy-1,2,3,7,8,8a(R)-hexahydronaphthyl-1(S)]-ethyl]-4(R)-hydroxy-3,4,5,6-tetrahydro-2H-pyran-2-one.

7. A compound of claim 2 wherein:
R is

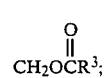

$R^1$ is $C_{1-10}$ alkyl; and
$R^3$ is phenylamino.

8. A compound of claim 7 which is 6(R)-[2-[8(S)-(2,2-dimethylbutyryloxy)-2(S)-methyl-6-phenylaminocarbonyloxymethyl-1,2,3,7,8,8a(R)-hexahydronaphthyl-1(S)]-ethyl]-4(R)-hydroxy-3,4,5,6-tetrahydro-2H-pyran-2-one.

9. A compound of claim 2 wherein:
R is

and
$R^1$ is $C_{1-10}$ alkyl.

10. A compound of claim 9 which is 6(R)-[2-[8(S)-(2,2-dimethylbutyryloxy)-2(S)-methyl-6-formyl-1,2,3,7,8,8a(R)-hexahydronaphthyl-1(S)]-ethyl]-4(R)-hydroxy-3,4,5,6-tetrahydro-2H-pyran-2-one.

11. A compound of claim 1 wherein:
$R^1$ is selected from:
(1) $C_{1-10}$ alkyl;
(2) $C_{3-8}$ cycloalkyl;
$R^3$ is selected from:
(1) $C_{1-10}$ alkyl;
(2) $C_{3-8}$ cycloalkyl;
(3) phenylamino; and
(4) substituted phenylamino in which the substituents are X and Y;
$R^4$ is hydrogen; and
a is a single bond.

12. A hypocholesterolemic, hypolipidemic pharmaceutical composition comprising a pharmaceutically acceptable carrier and a nontoxic effective amount of a compound as defined in claim 1.

13. A composition of claim 12 in which the compound is selected from:
(1) 6(R)-[2-[8(S)-(2,2-dimethylbutyryloxy)-2(S)-methyl-6-hydroxymethyl-1,2,3,7,8,8a(R)-hexahydronaphthyl-1(S)]-ethyl]-4(R)-hydroxy-3,4,5,6-tetrahydro-2H-pyran-2-one;
(2) 6(R)-[2-[8(S)-(2,2-dimethylbutyryloxy)-2(S)-methyl-6-carboxy-1,2,3,7,8,8a(R)-hexahydronaphthyl-1(S)]-ethyl]-4(R)-hydroxy-3,4,5,6-tetrahydro-2H-pyran-2-one;
(3) 6(R)-[2-[8(S)-(2,2-dimethylbutyryloxy)-2(S)-methyl-6-phenylaminocarbonyloxymethyl-1,2,3,7,8,8a(R)-hexahydronaphthyl-1(S)]-ethyl]-4(R)-hydroxy-3,4,5,6-tetrahydro-2H-pyran-2-one;
(4) 6(R)-[2-[8(S)-(2,2-dimethylbutyryloxy)-2(S)-methyl-6-formyl-1,2,3,7,8,8a(R)-hexahydronaphthyl-1(S)]ethyl]-4(R)-hydroxy-3,4,5,6-tetrahydro-2H-pyran-2-one.

14. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

15. A method of inhibiting cholesterol biosynthesis comprising the administration to a subject in need of such treatment a nontoxic thereapeutically effective amount of a compound of claim 1.

16. A method of claim 15 in which the compound is selected from:
(1) 6(R)-[2-[8(S)-(2,2-dimethylbutyryloxy)-2(S)-methyl-6-hydroxymethyl-1,2,3,7,8,8a(R)-hexahydronaphthyl-1(S)]ethyl]-4(R)-hydroxy-3,4,5,6-tetrahydro-2H-pyran-2one;
(2) 6(R)-[2-[8(S)-(2,2-dimethylbutyryloxy)-2(S)-methyl-6-carboxy-1,2,3,7,8,8a(R)-hexahydronaphthyl-1(S)]-ethyl]-4(R)-hydroxy-3,4,5,6-tetrahydro-2H-pyran-2-one;
(3) 6(R)-[2-[8(S)-(2,2-dimethylbutyryloxy)-2(S)-methyl-6-phenylaminocarbonyloxymethyl-1,2,3,7,8,8a(R)-hexahydronaphthyl-1(S)]-ethyl]-4(R)-hydroxy-3,4,5,6-tetrahydro-2H-pyran-2-one;
(4) 6(R)-[2-[8(S)-(2,2-dimethylbutyryloxy)-2(S)-methyl-6-formyl-1,2,3,7,8,8a(R)-hexahydronaphthyl-1(S)]ethyl]-4(R)-hydroxy-3,4,5,6-tetrahydro-2H-pyran-2-one.

* * * * *

UNITED STATES PATENT AND TRADEMARK OFFICE
CERTIFICATE OF CORRECTION

PATENT NO. : 4,857,547
DATED : August 15, 1989
INVENTOR(S) : W. F. Hoffman et al It is certified that error appears in the above-identified patent and that said Letters Patent is hereby corrected as shown below:

At column 19, line 36, after hydrogen insert -- $C_{1-3}$ alkyl or hydroxy $C_{2-3}$ alkyl; and --.

Signed and Sealed this

Twenty-third Day of October, 1990

Attest:

HARRY F. MANBECK, JR.

*Attesting Officer*      *Commissioner of Patents and Trademarks*